United States Patent
Fleischer et al.

(10) Patent No.: US 7,553,458 B2
(45) Date of Patent: Jun. 30, 2009

(54) ALCOHOL SENSOR USING THE WORK FUNCTION MEASUREMENT PRINCIPLE

(75) Inventors: Maximillian Fleischer, Hoehenkirchen (DE); Hans Meixner, Haar (DE); Tim Schwebel, Munich (DE); Elfriede Simon, Munich (DE)

(73) Assignee: Micronas GmbH, Freiburg (DE)

( * ) Notice: Subject to any disclaimer, the term of this patent is extended or adjusted under 35 U.S.C. 154(b) by 20 days.

(21) Appl. No.: 10/090,277

(22) Filed: Mar. 4, 2002

(65) Prior Publication Data
US 2002/0131898 A1    Sep. 19, 2002

(30) Foreign Application Priority Data
Mar. 5, 2001   (DE) ................. 101 10 471

(51) Int. Cl.
G01N 33/00   (2006.01)
(52) U.S. Cl. ............... 422/165; 422/50; 422/55; 422/56; 422/83; 422/88; 422/90; 422/91
(58) Field of Classification Search ............ 422/50, 422/55, 56, 83, 89, 88, 90, 91, 84, 165
See application file for complete search history.

(56) References Cited

U.S. PATENT DOCUMENTS

| | | | |
|---|---|---|---|
| 3,663,870 A * | 5/1972 | Tsutsumi et al. ........... 257/411 |
| 4,023,549 A | 5/1977 | Hewitt | |
| 4,151,060 A | 4/1979 | Isenberg | |
| 4,354,308 A | 10/1982 | Shimada et al. | |
| 4,633,704 A | 1/1987 | Tantram et al. | |
| 4,638,346 A * | 1/1987 | Inami et al. ........... 257/253 |
| 4,792,433 A | 12/1988 | Katsura et al. | |
| 5,635,628 A | 6/1997 | Fleischer et al. | |
| 5,879,527 A | 3/1999 | Kiesele et al. | |
| 6,041,643 A | 3/2000 | Stokes et al. | |
| 6,454,834 B1 | 9/2002 | Livingstone et al. | |
| 6,566,894 B2 | 5/2003 | Rump | |
| 6,935,158 B2 | 8/2005 | Serina et al. | |
| 2002/0092974 A1 | 7/2002 | Kouznetsov | |
| 2004/0112764 A1 | 6/2004 | Stokes et al. | |
| 2004/0133116 A1 | 7/2004 | Abraham-Fuchs et al. | |
| 2005/0035808 A1 | 2/2005 | Frerichs | |

FOREIGN PATENT DOCUMENTS

| | | | |
|---|---|---|---|
| DE | 4028062 | * | 3/1992 |
| DE | 4105598 | | 9/1992 |
| DE | 4239319 | | 4/1993 |
| DE | 4333875 | | 4/1995 |

(Continued)

OTHER PUBLICATIONS

Kienle et al., "Acticated Charcoal and its Industrial Application," Stuttgart : Enke, ISBN 3-432-90881-4, pp. 126 and 162-163, 1980.

(Continued)

*Primary Examiner*—Sam P Siefke
(74) *Attorney, Agent, or Firm*—O'Shea Getz P.C.

(57) ABSTRACT

An alcohol sensor having gas-sensitive layers made of polymers or inorganic oxides wherein a signal is read out by means of work function change which is produced in the form of a field-effect transistor.

4 Claims, 3 Drawing Sheets

FOREIGN PATENT DOCUMENTS

| | | |
|---|---|---|
| DE | 19534557 | 3/1997 |
| DE | 19613274 | 10/1997 |
| DE | 197 08 770 | 8/1998 |
| DE | 10245947 | 4/2004 |
| EP | 0952447 | 4/1998 |
| EP | 0 947 829 | 10/1999 |
| EP | 1 059 528 | 5/2000 |
| EP | 1104884 | 11/2000 |
| EP | 1103809 | 5/2001 |
| EP | 1 176 418 | 1/2002 |
| JP | 01059049 | 3/1989 |
| JP | 03131749 | 6/1991 |
| JP | 03259736 | 11/1991 |
| WO | WO 94/23288 | 10/1994 |
| WO | WO 96/01992 | 1/1996 |
| WO | WO 98/41853 | 9/1998 |
| WO | WO 03/050526 | 6/2003 |

OTHER PUBLICATIONS

Müller et al., "Adsorber for a Low Solvent Load," Intelligent Exhaust Air Cleaning Using Electric Current, Verfahrenstechnik, vol. 37, No. 9, pp. 30-31, 2003.

CCI Charcoal International : Activated Charcoal Textiles Given Uniform Brand Name of Zorflex, MaschinenMarkt, 2004, No. 17, p. 89.

Leu et al., "Evaluation of gas mixtures with different sensitive layers incorporated in hybrid FET structures," Sensors and Actuators B, Elsevier Sequoia, vol. 18-19, 1994, pp. 678-681.

Wöllenstein et al., "Cobalt oxide based gas sensors on silicon substrate for operation at low temperatures," Sensors and Actuators B: Chemical, Elsevier Sequoia, vol. 93, No. 1-3, Aug. 2003, pp. 442-448.

Gergintschew et al., "The capacitively controlled field effect transistor (CCFET) as a new low power gas sensor," Sensors and Actuators B: Chemical, Elsevier Sequoia, vol. 36, No. 1, Oct. 1996, pp. 285-289.

Paris et al., "57.5: Low Drift Air-Gap CMOS-FET Gas Sensor," Proceedings of IEEE Sensors, vol. 1 of 2, Conf. 1, Jun. 12, 2002, pp. 421-425, 2002, XP010605129, ISBN: 0-7803-7454-1.

Burgmair et al., "Humidity and temperature compensation in work function gas sensor FETs," Sensors and Actuators B, Elsevier Sequoia S.A., Lausanne, CH, vol. 93, No. 1-3, pp. 271-275, 2003.

Burgmair et al., "Field effect transducers for work function gas measurements : device improvements and comparison of performance," Sensors and Actuators B, Elsevier Sequoia S.A., Lausanne, CH, vol. 95, No. 1-3, pp. 183-188, 2003.

Covington, et al. "Combined smart chemFET/resistive sensor array," Proceedings of the IEEE, vol. 2., pp. 1120-1123, 2003.

Doll et al., "Modular System Composed of Hybrid GasFET Modules," ITG-Technical Report 126: Sensors-Technology and Application, VDE Verlag, Berlin, Germany, 1994, pp. 465-470, XP-000874734.

M. Lehmann, "Nanometre Dimensions in Bio and Gas Sensor Technology", MST News, Mar. 2004, pp. 43-47, XP-002379751.

Leu et al., "Evaluation of gas mixtures with different sensitive layers incorporated in hybrid FET structures," Sensors and Actuators B, Elsevier Sequoia, vol. 18-19, 1994, pp. 678-681.

Wöllenstein et al., "Cobalt oxide based gas sensors on silicon substrate for operation at low temperatures," Sensors and Actuators B: Chemical, Elsevier Sequoia, vol. 93, No. 1-3, Aug. 2003, pp. 442-448.

Gergintschew et al., "The capacitively controlled field effect transistor (CCFET) as a new low power gas sensor," Sensors and Actuators B: Chemical, Elsevier Sequoia, vol. 36, No. 1, Oct. 1996, pp. 285-289.

Fleischer et al., "Selective gas detection with high-temperature operated metal oxides using catalytic filters," Sensors and Actuators B, vol. 69, pp. 205-210, 2000.

Pohle et al., "Realization of a New Sensor Concept: Improved CCFET and SGFET Type Gas Sensors in Hybrid Flip-Chip Technology," Transducers, 12th International Conference on Solid-State Sensors, Actuators and Microsystems, Jun. 2003, vol. 1, 9, pp. 135-138.

Peschke et al., "Optimization of Sputtered SnO2 Films as Gas-sensitive Layers for Suspended-gate FETs", Sensors and Actuators B, 1991, pp. 157-160, XP-002379749.

Lampe et al., "GasFET for the detection of reducing gases", Sensors and Actuators B 111-112, 2005, pp. 106-110.

Mizsei et al., "Simultaneous Response of Work Function and Resistivity of some SnO2-based Samples to H2 and H2S", Sensors and Actuators B, 4 (1991), pp. 163-168, XP-002379750.

Doll et al., "Gas detection with work function sensors", Proceedings of the SPIE, SPIE, Bellingham, VA, US, vol. 3539, Nov. 1998, pp. 96-105, XP-002329891.

\* cited by examiner

FIG 3
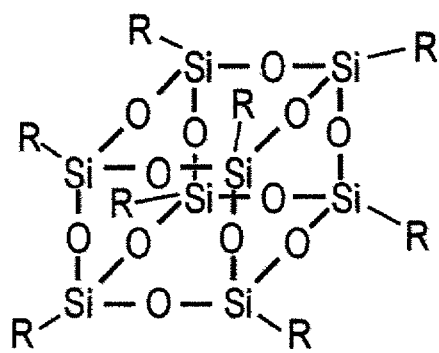
FIG 4A Polycyclopentylsilsesquioxane 60°C Sensor heating
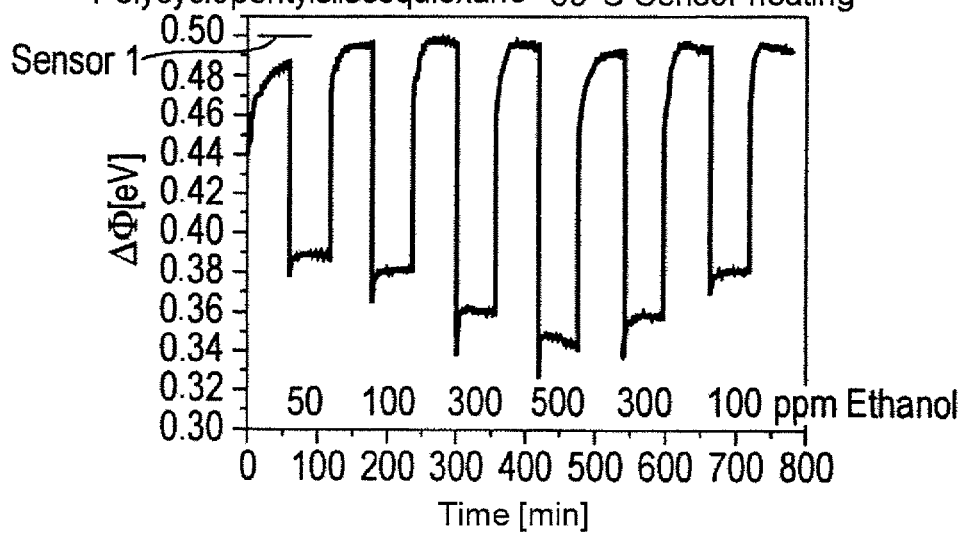
FIG 4B Polycyclopentylsilsesquioxane, <1 μm, 60°C
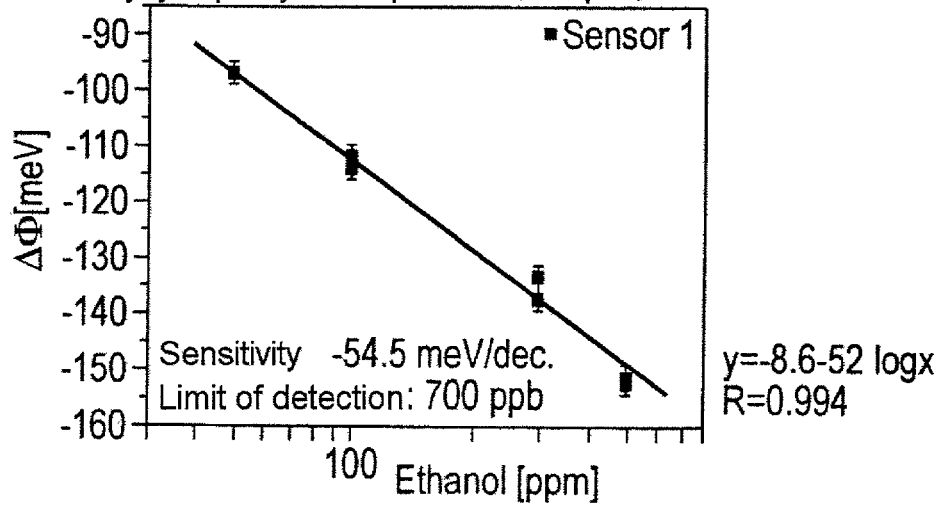
Sensitivity −54.5 meV/dec.
Limit of detection: 700 ppb
y=−8.6−52 logx
R=0.994

ALCOHOL SENSOR USING THE WORK FUNCTION MEASUREMENT PRINCIPLE

FIELD OF THE INVENTION

The invention relates to an alcohol sensor using the work function measurement principle which is produced in the form of a gas-sensitive field-effect transistor.

BACKGROUND OF THE INVENTION

There continues to be a need for inexpensive noninvasive alcohol sensors which determine the concentration of alcohol in various gas mixtures. Development of such a sensor is of importance since determining the alcohol concentration is necessary in various applications, for example detecting the blood alcohol value by determining ethanol in expired air or on the skin, in the membrane biotechnology sector, for example in fermenter processes, or in room air monitoring, for example for workplace safety. There are presently no sensors which have sufficiently long-term stability and which are inexpensive.

Determining the alcohol concentration in expired air for monitoring compliance with the blood alcohol limits is important particularly in the area of testing one's ability to drive in traffic. For this application it is necessary to develop inexpensive alcohol sensors in order to provide versatile expedient hand-operated instruments.

In the field of asthma diagnosis by means of nitrogen oxide detection in expired air, elimination of interfering effects is of great importance, for example eliminating effects of other gases which are present in high concentration. The ethanol concentration in expired air can rise up to 1500 ppm. Using an alcohol gas sensor, the concentration of ethanol can thus be determined in parallel, and thus the quality of the actual nitrogen oxide detection checked, and if appropriate, improved.

In addition to determining the alcohol concentration in expired air, alcohol content following alcohol consumption can also be detected on the skin. This provides the possibility for continuously measuring alcohol content without the active cooperation of the person being tested, and hence is ideal for monitoring persons who are, for example, in emergency medical situations.

Alcohol concentration measurements in the biotechnology sector are important for processes in which methanol is used as substrate in fermenter processes. Maintaining the methanol concentration precisely within a defined optimum range is of great importance for carrying out the fermentation and maintaining the fermentation processes. Monitoring the alcohol concentration in ambient air, for example in the workplace, is of great importance for ensuring workplace safety and compliance with MAC values. These are, with respect to ethanol, 1000 ppm, and, with respect to methanol, 200 ppm. Here also, the use of an inexpensive alcohol sensor or even of a personal alcohol alarm, is desirable.

Some known commercial alcohol sensors function primarily according to the resistive principle, where semiconductor materials are used as a gas-sensitive layer. A known gas-sensitive material for such sensors is tin oxide. Gallium oxide as a semiconductor material also has a very good sensitivity, and compared with tin oxide has a higher thermal long-term stability. By combining various filter layers over the gas-sensitive layers, highly selective sensors for detecting ethanol have been developed. Known materials for filter layers are, for example, silicon dioxide or aluminum oxide. These developments have been able to suppress cross-sensitivities to interfering gases. However, a disadvantage of semiconductor alcohol sensors is the power requirement for the obligatory sensor heating, and for this reason, sensor variants for use as modular elements or in battery-operated instruments, for example a cell telephone, are not currently possible.

In addition to the foregoing, electrochemical alcohol sensors are known which are also used as hand-operated instruments for measuring alcohol in the breath. A disadvantage of these sensors is that they have only a limited life and are costly.

In the area of optical methods of measurement, there are infrared sensors for determining alcohol in expired air, or gas sensors which are based on the principle of cataluminescence. Infrared detection using bandpass filters frequently shows a high cross-sensitivity to various hydrocarbons and gases, in which case selective detection of alcohols under actual conditions cannot be guaranteed. Although cataluminescence-based alcohol sensors can differentiate between various alcohols, for example between ethanol and butanol, they cannot differentiate between alcohols and ketones. Furthermore, these optical methods of measurement are also very expensive.

SUMMARY OF THE INVENTION

It is an object of the present invention to provide an inexpensive, portable alcohol sensor. The invention is based on the finding that using a combination of a sensor which is read-off by the work function measurement principle, and is produced in the form of a field-effect transistor, results in important advantages with respect to the energy supply. The particular selection of polymers or inorganic metal oxides for use as a sensitive layer gives a further optimization of such an alcohol sensor. The essential advantages of the present invention are the range of operating temperatures which are between room temperature and a maximum of 60° C. As a result, measurements can be carried out with reduced heating energy requirements which makes development of an inexpensive sensor possible and opens up applications involving low-power electrical supply. Furthermore, the sensor offers the advantages of selecting sensitive materials having a greater bandwidth that can be prepared relatively simply. The gas sensors can be coated with a gas-sensitive layer of polymers, for example polysiloxane, polyetherurethane, polycarbonate or calixarenes. Furthermore, metal oxides, for example scandium oxide, also have alcohol-sensitive properties. By combining different gas-sensitive layers which respond to different gases, the effects of temperature and moisture, for example, can be eliminated from the alcohol measurement.

BRIEF DESCRIPTION OF THE DRAWINGS

The present invention is described in greater detail below and in connection with the drawings, in which:

FIG. 3 illustrates the hypothetical structure of polysilsesquioxane;

FIGS. 4A and 4B illustrate the change in work function at differing ethanol concentrations in synthetic air at 28% relative humidity, and the ethanol characteristic line at a temperature of 60° C.;

DETAILED DESCRIPTION OF THE INVENTION

The gas sensors of the present invention can be coated by polymers, for example polysiloxanes, polyetherurethanes, polycarbonates or calixarenes. In addition, metal oxides, for example scandium oxide, also display alcohol-sensitive properties. Reading-out the work function via a newly developed field-effect transistor (FET) enables a smaller and more cost-effective construction of this gas sensor system.

Figure 1:
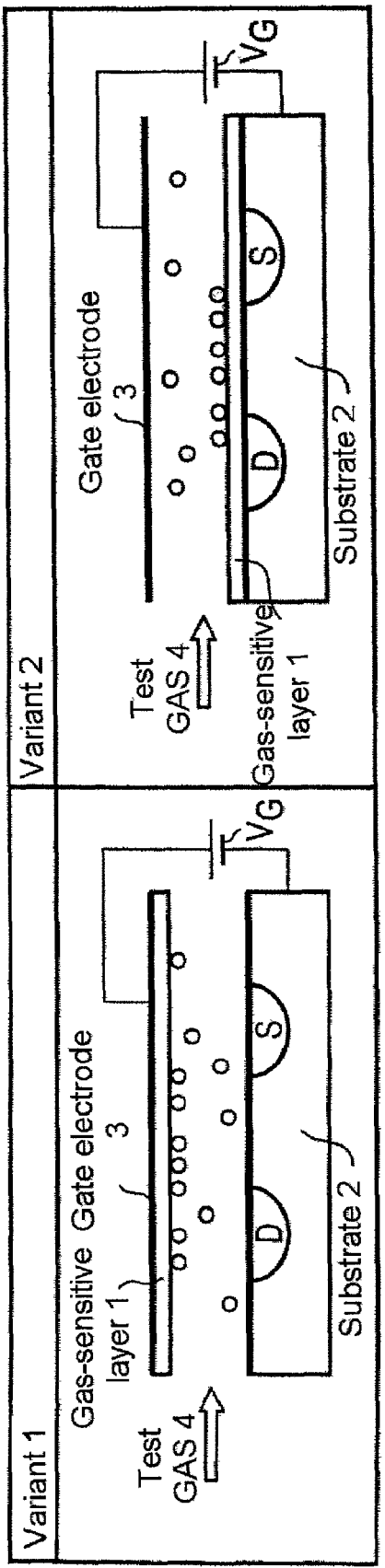
FIG. 1 illustrates the concept of a gas-sensitive field-effect transistor in two variations.

With these objectives, FIG. 1 shows two variants for the structure of the field-effect transistor. The gas-sensitive layer 1 can, in accordance with variant 1, be applied separately to a substrate and be situated opposite the gate of the field-effect transistor. In accordance with the FIG. 1, the gas-sensitive layer 1 is situated at a gate electrode 3. Variant 2 in FIG. 1, shows a layer structure which is considerably simpler in terms of method of construction. In this case, the gas-sensitive layer 1 is applied directly to the gate of the field-effect transistor, that is to say on the side of the substrate on which the source and drain areas are placed.

By combining various layers in a sensor arrangement, the temperature and moisture effects relative to the target gas sensor signal to be measured can be determined. If a moisture-sensitive layer and an alcohol-sensitive layer are used simultaneously in a sensor arrangement, or in a field-effect transistor, this makes it possible for direct signal balancing and specific evaluation of the actual alcohol signal. Thus, an alcohol sensor in which the cross-sensitivities are virtually eliminated can be developed and brought into production.

Figure 2:
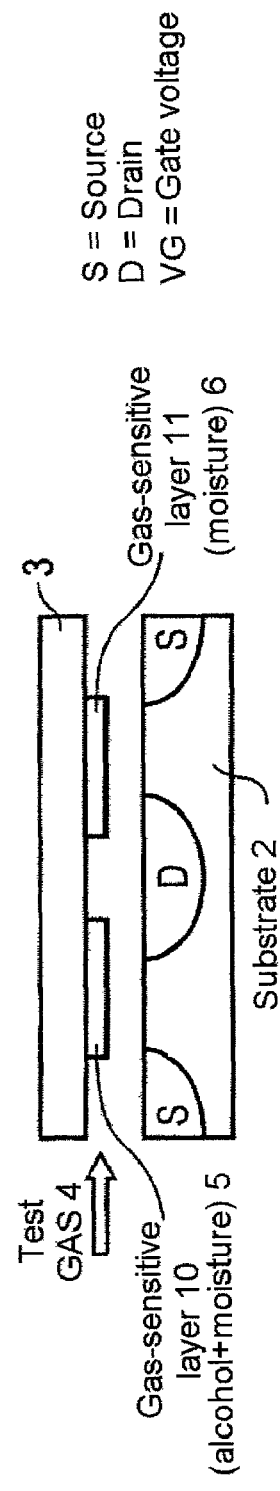
FIG. 2 illustrates a field-effect transistor in a dual construction to compensate for the effect of moisture, and having moisture- and alcohol-sensitive layers.

FIG. 2 illustrates two different gas-sensitive layers 5 and 6. One layer is sensitive not only to alcohol but also to moisture. The other layer is only sensitive to moisture, so that its signal can be used for correction to eliminate the effect of moisture on the actual signal used for the purpose of alcohol detection. The gas-sensitive layers 5 and 6 are each positioned opposite a source-drain area.

By means of the sensor described, it is possible to develop an alcohol sensor having a multiplicity of applications in an inexpensive form. The applications are, for example, alcohol measurements in expired gas, in fermenter processes or, for example, for workplace safety. Important features of the present invention are the combination of the principle of measuring the change in work function and the use of specific material layers to determine alcohol in gases. By using a second gas-sensitive layer which reacts, for example, solely to moisture, cross-sensitivities, in particular in the breath, can be compensated for. It is thus possible to obtain the alcohol concentration via a sensor having low operating power consumption and low manufacturing costs.

FIG. 3 shows the structure of polysilsesquioxane. Studies of various compounds have found that polymers such as polysiloxanes are particularly suitable for direct measurement of ethanol by means of work function change. In this case, polysilsesquioxane derivatives, which distinguish themselves among the class of polysiloxanes by their particular structure and stoichiometric composition ($RSiO_{1.5}$), are particularly suitable.

Figure 5:
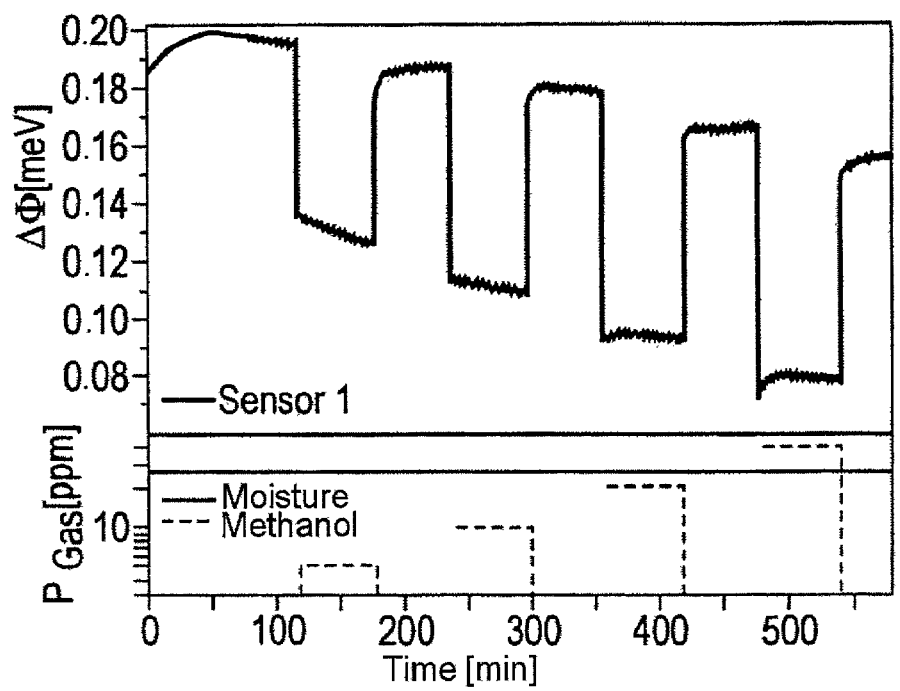
FIG. 5 illustrates the change in work function of polycyclopentylsilsesquioxane at differing methanol concentrations at a sensor temperature of 60° C. for a measurement in synthetic air of 30% relative humidity.

Work function measurements and the ethanol characteristic of polycyclopentyl-silsesquioxane are shown in the FIGS. 4A and 4B. In FIG. 4A it may be noted that the sensor signal decreases with increasing ethanol concentration. The sensitivity of this material, at a sensor temperature of 60° C., is −54.4 meV per decade ethanol concentration, with very narrow response times. The gas-sensitive layer shows cross-sensitivities to acetone at −13 meV per decade of acetone concentration, and a very low nitrogen oxide sensitivity of −12 meV at 2 ppm of nitrogen oxide. Nitrogen oxide is present at between 3 ppb and 10 ppb in usual expired air. In addition, a low sensitivity to moisture was found. Polycyclopentylsilsesquioxane, in addition to the high ethanol sensitivity, shows a sensitivity to methanol which is lower, but nevertheless good. FIG. 5 shows the change in work function with differing methanol concentrations. The sensitivity of the sensor is −26 meV per decade of methanol concentration at a sensor temperature of 60° C. The sensitivity is thus lower than for ethanol by a factor of 2.

Scandium oxide ($Sc_2O_3$) has been identified as a further methanol-sensitive material. To study the gas sensitivities, two samples were produced using a scandium thick-layer paste. The base element of the sensor consists of a ceramic aluminum oxide element onto which a platinum electrode is applied over the whole surface. This electrode serves for the electrical contacting of the Kelvin system. The scandium oxide paste was applied using a brush. 0.15 g of $Sc_2O_3$ and about 7 g of organic binder, for example ethylcellulose in terpineol, were used. On account of the high solubility of scandium oxide in the binder, very homogeneous layers can be produced. The resultant layer thicknesses are in the range of a few hundred micrometers. The ceramic element, after application, is dried at 80° C. for about 30 minutes and then tempered at 950° C. for about 15 minutes. The organic binder in the paste is decomposed by this and formation of a polycrystalline structure is made possible. Adhesion of these layers to the substrate is improved by burning in the layer at temperatures above 1200° C. When viewed by light microscopy, a porous structure can be seen. Compared with the geometric surface area, the effective absorption area is much greater. The interaction with gases is promoted.

Figure 6:
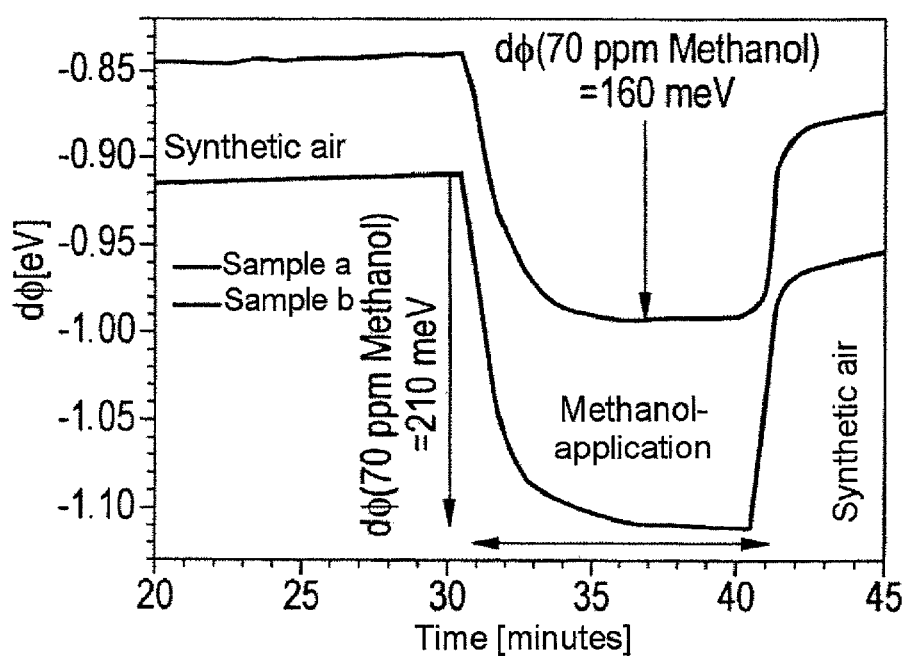
FIG. 6 illustrates the time course in the work function difference between two $Sc_2O_3$ samples for application of 70 ppm of methanol at room temperature in synthetic air of 40% relative humidity.

FIG. 6 shows the course of the work function difference between $Sc_2O_3$ for an application of 70 ppm of methanol at room temperature in synthetic air. The course of measurement shows qualitatively the same behavior for both samples. The measurement shown applies to room temperature. When 70 ppm of methanol in synthetic air are applied, the work function difference between the gold reference electrode used here and the $Sc_2O_3$ element increases.

The sample (a) in FIG. 6 reacts with a contact potential difference of 160 meV, and sample (b) even achieves 210 meV. The differing sensitivity of the two samples can be based on (i) the non-reproducibility of the preparation of the layers or, (ii) the differing layer thicknesses and differing crystal structures which lead to a difference in absorption behavior. Depending on the use, the described organic and inorganic layers can be used as an alcohol sensor for detecting ethanol in expired air, or for detecting methanol in fermenter processes. Furthermore, they serve for detecting the amount of gas in the alcohol measurement both for ethanol and for methanol, for example in workplace safety.

We claim:

1. An alcohol sensor utilizing a work function measurement principle comprising at least one gas-sensitive field-effect transistor which comprises at least one substrate having source and drain areas and at least one gate electrode located at a distance from a gate region between the source and drain areas, said gate electrode being associated with a gas-sensitive layer comprising a polymer or an inorganic metal oxide and wherein the layer is applied separately to the substrate such that it is substantially opposite a gate region of the field-effect transistor thereby forming a gap there between, wherein the gas-sensitive layer comprises a polymer and is selected from the group consisting of polysiloxane or and a polysilsesquioxane derivative, wherein the polysilsesquioxane derivative is polycyclopentylsilsesquioxane.

2. An alcohol sensor utilizing a work function measurement principle comprising:

at least one gas-sensitive field-effect transistor which comprises at least one substrate having source and drain areas, at least one gate electrode located at a distance from the source and drain areas, and a gas-sensitive layer, wherein the gas-sensitive layer comprises polycyclopentylsilsesquioxane.

3. The alcohol sensor of claim 2, where the gas-sensitive layer is adjacent to the gate electrode.

4. The alcohol sensor of claim 2, where the gas-sensitive layer is adjacent to the source and drain areas.

* * * * *